United States Patent [19]

Harris

[11] Patent Number: 4,490,532
[45] Date of Patent: Dec. 25, 1984

[54] SYNTHESIS OF 2-[1-(2,5-DIMETHYLPHENYL)ETHYLSULFONYL]PYRIDINE-1-OXIDE HERBICIDE AND INTERMEDIATES THEREFOR

[75] Inventor: John W. Harris, Guelph, Canada

[73] Assignee: Uniroyal Ltd., Don Mills, Canada

[21] Appl. No.: 172,603

[22] Filed: Jul. 28, 1980

[51] Int. Cl.³ .......................................... C07D 211/54
[52] U.S. Cl. ................... 546/294; 570/194; 546/290; 568/67
[58] Field of Search ............... 568/793, 67; 570/194; 546/294, 290

[56] References Cited

U.S. PATENT DOCUMENTS

| | | | |
|---|---|---|---|
| 2,147,400 | 2/1939 | Clark et al. | 568/67 |
| 2,349,779 | 5/1944 | Zoeren | 570/194 |
| 2,516,971 | 8/1950 | Galitzenstein | 570/194 |
| 3,780,117 | 12/1973 | Bruson et al. | 570/194 |
| 3,960,542 | 6/1976 | Plant et al. | 546/294 |
| 4,019,893 | 4/1977 | Plant et al. | 546/294 |
| 4,120,692 | 10/1978 | Plant et al. | 546/294 |

FOREIGN PATENT DOCUMENTS 597674  5/1976  U.S.S.R. ............... 546/294

OTHER PUBLICATIONS

Reid, Organic Chemistry of Bivalent Sulfur, vol. II, p. 21 and vol. I, p. 127, Chem. Publishing Co., New York, 1960.
Baitman et al., J. Org. Chem., vol. 41, No. 5, 1976, pp. 776–780.
Kuliev et al., Org. Khim. (1971), 7, 992.

Primary Examiner—Henry R. Jiles
Assistant Examiner—Robert C. Whittenbaugh
Attorney, Agent, or Firm—Marvin Bressler; John A. Shedden

[57] ABSTRACT

Hydrogen chloride is passed into p-xylene and acetaldehyde to form bis-1-chloroethyl ether; the latter is converted to 2-(1-chloroethyl)-1,4-dimethylbenzene by the action of sulfuric acid and hydrogen chloride. Alkali metal hydrogen sulfide in aqueous methanol or ethanol converts the 2-(1-chloroethyl)-1,4-dimethylbenzene to alpha,2,5-trimethylbenzenemethanethiol; the sodium salt of the latter reacted with 2-chloropyridine-1-oxide yields 2-[1-(2,5-dimethylphenyl)ethylthio]pyridine-1-oxide which is then oxidized with hydrogen peroxide and alkali metal tungstate or tungstic acid to form 2-[1-(2,5-dimethylphenyl)ethylsulfonyl]pyridine-1-oxide.

5 Claims, No Drawings

SYNTHESIS OF 2-[1-(2,5-DIMETHYLPHENYL)ETHYLSULFONYL]PYRIDINE-1-OXIDE HERBICIDE AND INTERMEDIATES THEREFOR

This invention relates to the synthesis of 2-[1-(2,5-dimethylphenyl)ethylsulfonyl]pyridine-1-oxide herbicide and intermediates therefor.

More particularly the invention relates to one or more of the following steps, wherein I is acetaldehyde, II is bis-1-chloroethyl ether, III is p-xylene, IV is 2-(1-chloroethyl)-1,4-dimethylbenzene, M is an alkali metal, V is alpha,2,5-trimethylbenzenemethanethiol (believed to be a new compound), VI is alkali metal salt of alpha,2,5-trimethylbenzenemethanethiol, VII is 2-chloropyridine-1-oxide, VIII is 2-[1-(2,5-dimethylphenyl)ethylthio]pyridine-1-oxide, and IX is the desired herbicide, 2-[1-(2,5-dimethylphenyl)ethylsulfonyl]pyridine-1-oxide:

Step A

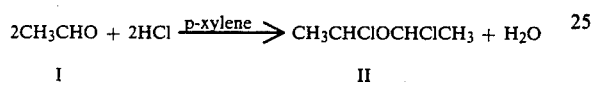

Step B

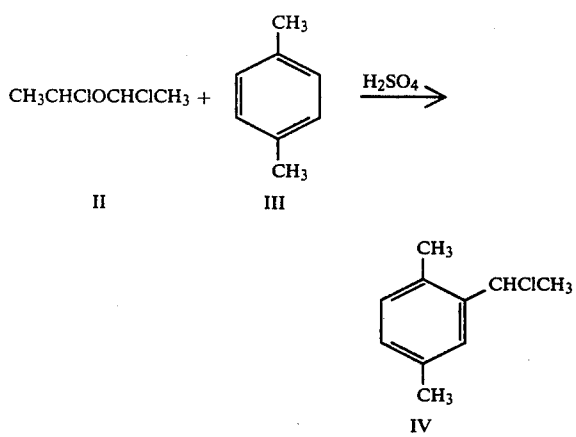

Step C

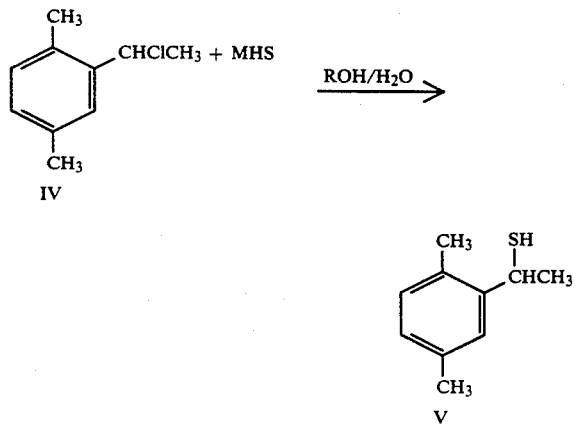

M indicates alkali metal

Step D

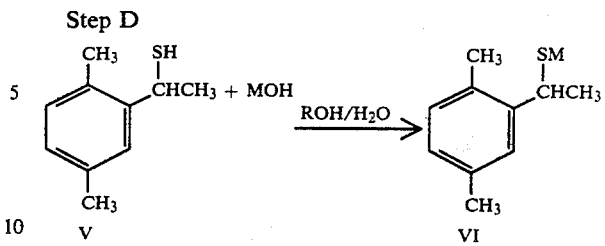

Step E

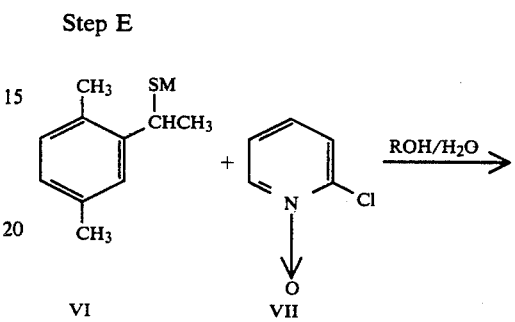

Step F

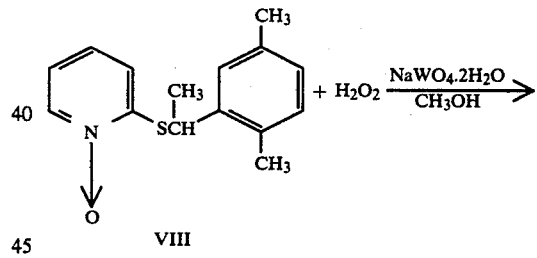

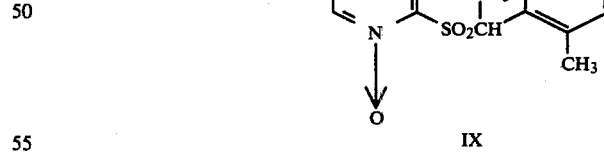

In one aspect, the invention involves the reaction of acetaldehyde (I) or a substance decomposable under the reaction conditions to yield aldehyde I, with hydrogen chloride in p-xylene, affording bis-1-chloroethyl ether (II) and water. After the aqueous phase is removed, sulfuric acid is added to promote a reaction between the ether II and p-xylene (III) giving 2-(1-chloroethyl)-1,4-dimethylbenzene (IV). Chloride IV is converted to alpha,2,5-trimethylbenzenemethanethiol (V) with alkali metal hydrogen sulfide in alcohol. The addition of aqueous alkali metal hydroxide to the alcoholic solution of thiol V affords the thiol alkali metal salt VI, which is coupled with 2-chloropyridine-1-oxide (VII) giving 2-[1-(2,5-dimethylphenyl)ethylthio]pyridine-1-oxide (VIII).

Sulfide VIII is oxidized with hydrogen peroxide in methanol, or a mixture of methanol and dichloromethane, in the presence of a catalyst, for example, an alkali metal tungstate or tungstic acid, affording sulfone IX.

In U.S. Pat. Nos. 3,960,542, June 1, 1976, Plant et al (Example 6) and 4,019,893, Apr. 26, 1977, Plant et al (Example 6), the use of chloride IV as an intermediate in the preparation of the herbicide 2-[1-(2,5-dimethylphenyl)ethylsulfonyl]pyridine-1-oxide (IX) by the following process is disclosed:

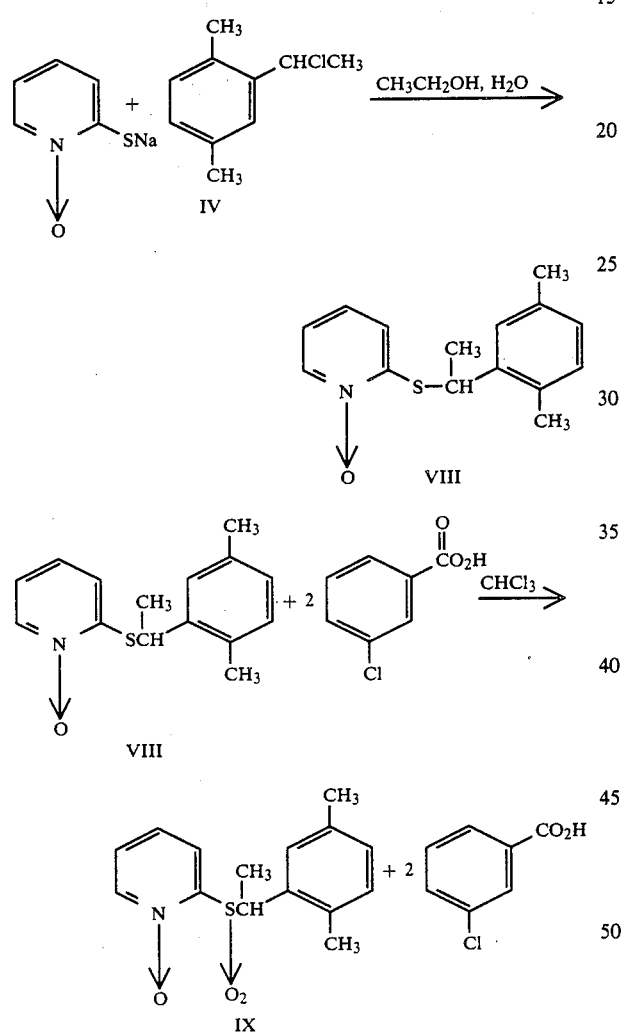

U.S. Pat. Nos. 3,960,542 and 4,019,893 also give examples of the oxidation of 2-thiopyridine-1-oxides to the corresponding sulfonyl compounds with hydrogen peroxide in water and acetic acid in the presence of sodium tungstate. According to these patents (Col. 4, lines 52 to 54 of U.S. Pat. No. 3,960,542 and Col 5, lines 4 to 8 of U.S. Pat. No. 4,019,893) "Temperature and time are a function of the sulfide employed with the range varying from 50° to reflux in the case of water and acetic acid." By contrast, temperatures of less than 50° are preferred for the oxidation of sulfide VIII by the present process, since the use of temperatures greater than 50° results in severely decreased yields of sulfone IX.

Processes related to 2-(1-chloroethyl)-1,4-dimethylbenzene (IV) are as follows:

Process A'

U.S. Pat. No. 2,516,971, Aug. 1, 1950, Galitzenstein et al discloses the zinc chloride catalyzed chloroethylation of alkylated benzene compounds by the following processes:

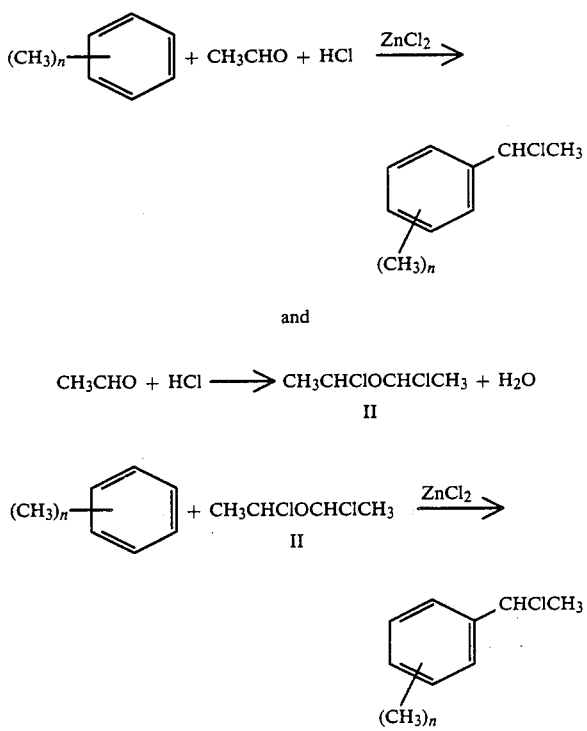

Although the chloroethylations of o- and m-xylenes by the above processes proceed in about 70% yield, the inventors state (Col. 1, lines 32 and 33) that, "The reaction with p-xylene results in very small yields only." By contrast, the present process for the chloroethylation of p-xylene (Steps A and B) proceeds in about 48% yield based on acetaldehyde and 60% yield based on p-xylene consumed.

Process B'

The synthesis of 2-(1-chloroethyl)-1,4-dimethylbenzene (IV) has been reported by D. S. Noyce, B. Bartman, E. Gordon, M. Gonzalez-Kutas and B. Sandel, J. Org. Chem., (1976), 41, 776–80. The synthesis involved the reaction of thionyl chloride with alpha, 2,5-trimethylbenzenemethanol (X)

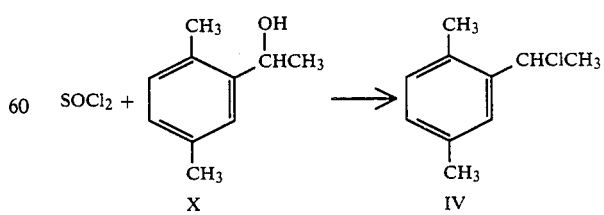

which was prepared according to the following method reported by A. M. Kuliev, B. M. Mirzoev, H. Nguyen, and V. M. Farzaliev, Zh. Org. Khim, (1971), 7, 992:

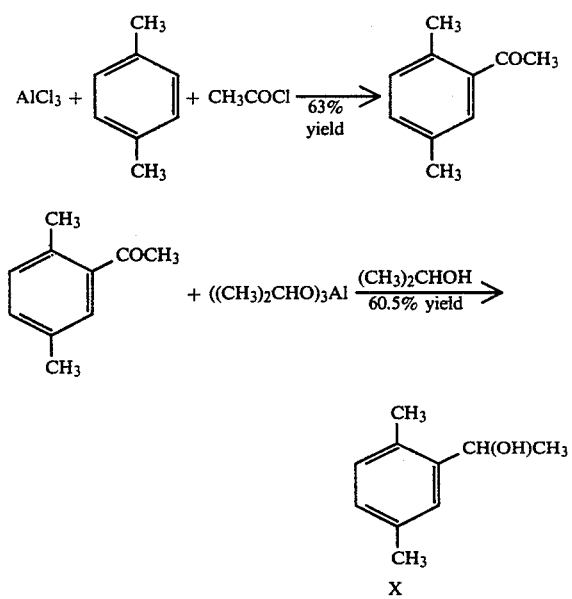

The present process affords a considerably higher yield of chloride IV than does Process A'. In U.S. Pat. No. 2,516,971 referred to previously, disclosing Process A', the zinc chloride catalyzed chloroethylation of polymethyl substituted benzenes, it is stated that, "The reaction with p-xylene results in very small yields only." By contrast, the present process for the sulfuric acid catalyzed chloroethylation of p-xylene (Steps A and B) proceeds in about 48% yield based on acetaldehyde and 60% yield based on p-xylene consumed.

The present process for the preparation of chloride IV (Steps A and B) requires only one reaction vessel. However, process B' involves three steps (acetylation, reduction, and chlorination) and requires three reaction vessels.

The present process requires much cheaper reagents ($H_2SO_4$, $CH_2CHO$) than Process B' ($AlCl_3$, $CH_3COCl$).

The oxidation of one mole sulfide VIII with 2 moles m-chloroperbenzoic acid, according to the examples in U.S. Pat. Nos. 3,960,542 and 4,019,893, affords two moles m-chlorobenzoic acid as by-product which must be disposed of. The present process uses a considerably cheaper oxidizing agent, hydrogen peroxide, which decomposes to water.

The present process uses methanol or a mixture of methanol and dichloromethane as solvents for the alkali metal tungstate catalyzed oxidation of sulfide VIII to sulfone IX, rather than water and acetic acid, as suggested in U.S. Pat. Nos. 3,960,542 and 4,019,893. Methanol and dichloromethane are more advantageous solvents than acetic acid since their boiling points (dichloromethane b.p. 40°–41°, methanol b.p. 65°) are lower than the boiling point of acetic acid (118.5°). Thus their recovery is easier and cheaper, and they are less likely than acetic acid to contaminate the final product. Whereas oxidation reaction temperatures of 50° to reflux are recommended in the two patents mentioned above (for the oxidation of 2-thiopyridine-N-oxides in water and acetic acid with hydrogen peroxide), the present process uses temperatures less than 50°, preferably 40°–45°, for the oxidation of sulfide VIII. The yield of sulfone IX is considerably decreased when temperatures of greater than 50° are used in the present process.

In more detail in the aspect of the present invention identified as Step A, hydrogen chloride is passed into a stirred solution of p-xylene and acetaldehyde (I), or a substance which is decomposable, under the reaction conditions, to yield aldehyde I (such as paraldehyde), at a temperature in the range −10° to +20° (preferably 5° to 10°). This gives bis-1-chloroethyl ether (II) and water. A cosolvent, such as petroleum ether or dichloromethane, may be used in this step or is added with additional p-xylene in Step B. The lower aqueous phase is removed from the reaction mixture. This is desirable in order to obtain optimal yields in Step B. In order to facilitate the removal of the relatively small aqueous phase, a low molar ratio of p-xylene to aldehyde I, in the range 1:1 to 2:1, is used in Step A. This ratio can be increased at the beginning of Step B.

The cosolvent is used in order to prevent the freezing of the p-xylene (f.p. 13°–14°), especially at the low temperatures which are used in Step B. A volume of cosolvent which is about equal to the volume of the acetaldehyde in the reaction mixture is satisfactory.

In the aspect of the invention referred to as Step B, the concentrations of p-xylene (III) and cosolvent in the reaction mixture are adjustd to the desired levels. Molar ratios of xylene (III) used in Step B to aldehyde I (Step A) of, for example, up to 8:1 are suitable. The preferred molar ratio is in the range 3:1 to 4:1. Hydrogen chloride is passed into the stirred reaction mixture and 1.0 to 1.2 equivalents (based on aldehyde I, Step A) of concentrated sulfuric acid are added during 0.5 to 1.0 hours while the temperature of the mixture is maintained in the range −10° to +10° (preferably −5° to +5°). After the addition, the mixture is stirred and cooled for an interval of 0.5 to 2.0 hours (preferably 0.75 to 1.5 hours) then it is quenched with water (3 to 5 ml per ml of concentrated sulfuric acid) and neutralized with base, such as ammonium hydroxide or alkali metal hydroxide. Phase separation occurs more rapidly when ammonium hydroxide is used. Isolation and fractional distillation of the organic phase afford recovered cosolvent and xylene (III) and the desired product, 2-(1-chloroethyl)-1,4-dimethylbenzene (IV). Product IV is obtained in yields of up to 48%, based on acetaldehyde, and 60%, based on xylene III consumed.

It is necessary to pass hydrogen chloride into the reaction mixture in Step B in order to obtain optimal yields of product IV. The yield of IV, based on aldehyde I, is decreased by about 10% if the hydrogen chloride is omitted.

In the aspect of the invention called Step C, 2-(1-chloroethyl)-1,4-dimethylbenzene (IV) is added to a stirred solution of 1.2 to 1.5 equivalents of alkali metal hydrogen sulfide in a 1:2 (V/V) mixture of water and alcohol (ethanol or methanol, preferably ethanol), then the resulting mixture is stirred at a temperature in the range 10°–40° (preferably 20°–30°) for 2 to 5 hours (preferably 2.5 to 3.5 hours). This yields a solution of alpha,2,5-trimethylbenzenemethanethiol (V) in aqueous alcohol.

A minimum of solvent mixture is used, typically 2 to 3 ml per gram of chloride IV, in order to limit the solvolysis of chloride IV.

In Step D, the reaction mixture (Step C) is diluted with 1 to 3 ml of water and 0.5 to 1 ml of alcohol per gram of chloride IV (Step C). Alkali metal hydroxide (the same number of equivalents as alkali metal hydrogen sulfide in Step C) is added while the temperature of the reaction mixture is maintained in the range 10°–40°

(preferably 20°–30°). A solution of alpha,2,5-trimethylbenzenemethanethiol, alkali metal salt (VI) in aqueous alcohol is obtained.

In the form of the invention known as Step E, a solution of 2-chloropyridine-1-oxide (VII) in water, typically 1 to 3 ml of water per gram of VII, is added to the solution of thiol alkali metal salt VI (Step D). The mixture is stirred and heated at a temperature in the range 50° to 80° for 50 to 90 minutes. The mixture is cooled to room temperature in order to precipitate the product, 2-[1-(2,5-dimethylphenyl)ethylthio]pyridine-1-oxide (VIII). Water is added, typically 5 to 10 ml per gram of compound VII, in order to keep the inorganic salts in solution and to accelerate the precipitation of the product, VIII. Compound VIII is isolated by filtration in yields of up to 88% based on chloride IV or 2-chloropyridine-1-oxide (VII).

In the final step, Step F, a mixture of sulfide VIII and a catalyst such as an alkali metal tungstate or tungstic acid (2 to 15% by weight based on VIII) in methanol (3 to 6 ml, per gram of VIII) or in methanol and dichloromethane (3 to 6 ml, per gram of VIII, of a 0.5:1 to 3:1 (v/v) methanol-dichloromethane solvent mixture), is stirred and heated to between 35° to 50° (preferably 40° to 45°). Hydrogen peroxide (for example 35% or 50%), 2.0 to 2.5 equivalents, is added during 20 to 80 minutes. After the addition is completed the reaction mixture is stirred at 40° to 45° for 1 to 6 hours. The reaction proceeds more rapidly when a methanol-dichloromethane solvent mixture is used than when methanol alone is used as a solvent. The yield in this reaction is severely decreased if the oxidation is carried out at temperatures greater than 50°.

When methanol is used as the reaction solvent, the product is isolated by allowing the mixture to cool to room temperature, and water (2 to 5 ml per gram of sulfide VIII) is added to dissolve the catalyst and to precipitate the product, sulfone IX. When a mixture of methanol and dichloromethane is used, the dichloromethane is removed by distillation before the water is added. Sulfone IX is isolated by filtration and washed with water. Yields of up to 85% of sulfone IX, based on sulfide VIII, are obtained.

The following examples will serve to illustrate the practice of the invention in more detail.

EXAMPLE 1

Gaseous hydrogen chloride was passed into a cold (5° to 10°), rapidly stirred solution of 240 ml (1.96 m) p-xylene and 54.75 ml (0.98 m) acetaldehyde (I) until the conversion (monitored by means of nuclear magnetic resonance spectroscopy) of aldehyde I to bis-1-chloroethyl ether (II) was complete. The lower, aqueous phase was removed and 20 ml (1.96 m) p-xylene (III) and dichloromethane (55 ml) were added. The reaction mixture was cooled and maintained in the temperature range 0° to 5° while the introduction of hydrogen chloride and rapid stirring were continued. Concentrated sulfuric acid, 54.75 ml (1.03 m), was added during 55 minutes. After the addition was completed, stirring and cooling were continued for 45 minutes. The reaction mixture was then quenched with 200 ml water. The resulting mixture was neutralized with concentrated ammonium hydroxide and the organic phase was collected. Dichloromethane (40 ml) was distilled from the organic phase at atmospheric pressure. Fractional distillation of the remainder of the product mixture at reduced pressure (about 30 mm Hg) afforded 333.3 g (3.14 m) xylene III and 78.2 g (0.47 m) chloride IV. The isolated yield of chloride IV was 48% based on aldehyde I or 60% based on consumed xylene III.

EXAMPLE 2

Gaseous hydrogen chloride was passed into a cold (5° to 10°), rapidly stirred solution of 240 ml (1.96 m) p-xylene, 54.75 ml (0.98 m) acetaldehyde (I) and 55 ml petroleum ether (30°–60° fraction) until the conversion (monitored by means of nuclear magnetic resonance spectroscopy) of aldehyde I to bis-1-chloroethyl ether (II) was complete. The lower, aqueous phase was removed and 240 ml (1.96 m) p-xylene (III) was added. The reaction mixture was cooled and maintained in the temperature range 0° to 5° while the introduction of hydrogen chloride and rapid stirring were continued. Concentrated sulfuric acid, 54.75 ml (1.03 m), was added during 40 minutes. After the addition was complete, stirring and cooling were continued for 90 minutes. The reaction mixture was then quenched with 200 ml water. The resulting mixture was neutralized with concentrated ammonium hydroxide and the organic phase was collected. Petroleum ether (37 ml) was distilled from the organic phase at atmospheric pressure. Fractional distillation of the remainder of the product mixture at reduced pressure (about 30 mm Hg) afforded 317.6 g (3.00 m) xylene III and 82.3 g (0.49 m) chloride IV. The isolated yield of chloride IV was 50% based on aldehyde I or 53% based on consumed xylene III.

Additional examples, which were carried out under similar conditions, with various proportions of reactants and solvents, are summarized in Table A.

TABLE A

Steps A and B
Preparation of 2-(1-Chloroethyl)-1,4-Dimethylbenzene (IV)

| | Reactants and Solvents | | | | | | Yield of IV (%) | |
|---|---|---|---|---|---|---|---|---|
| | Acetaldehyde | | p-Xylene | | Sulfuric Acid | | Cosolvent | Based on Acetaldehyde (I) | Based on p-Xylene Consumed |
| Example | ml | (m) | ml | (m) | ml | (m) | (ml) | | |
| 3 | 20 | (0.36) | 160 | (1.31) | 20 | (0.38) | $CH_2Cl_2$ (20) | 50 | 53 |
| 4 | 20 | (0.36) | 160 | (1.31) | 20 | (0.38) | $CH_2Cl_2$ (30) | 42 | 56 |
| 5 | 54.75 | (0.98) | 480 | (3.92) | 54.75 | (1.03) | $CH_2Cl_2$ (75) | 46 | 69 |
| 6 | 20 | (0.36) | 160 | (1.31) | 20 | (0.38) | pet ether (20) | 50 | 46 |
| 7 | 20 | (0.36) | 320 | (2.61) | 20 | (0.38) | $CH_2Cl_2$ (20) | 48 | 57 |

EXAMPLE 8

An aqueous solution of sodium hyrogen sulfide was prepared by passing hydrogen sulfide into a stirred solution 3.6 g ($9.0 \times 10^{-2}$ m) sodium hydroxide in 10.0 ml water. The mixture was diluted with 20 ml 95% ethanol and 10.0 g ($5.95 \times 10^{-2}$ m) chloride IV were added. Stirring of the mixture at 25°–28° for 3.0 hours afforded a solution of alpha,2,5-trimethylbenzenemethanethiol (V). This solution was diluted with 20 ml water and 10 ml 95% ethanol. The solution was stirred and 7.2 g of a 50% aqueous solution of sodium hydroxide ($9.0 \times 10^{-2}$ m) were added during 5 minutes. The mixture was then stirred an additional 5 minutes at 25°–28°. A solution of 7.68 g ($5.95 \times 10^{-2}$ m) 2-chloropyridine-1-oxide (VII) in 20 ml water was added during 5 minutes, and the resulting mixture was stirred and heated at 65° for 80 minutes. The mixture was cooled to 5°–10° and 50 ml cold water added to accelerate the precipitation of the product. Filtration afforded 13.5 g of sulfide VIII. The yield of sulfide VIII was 88% based on chloride IV or 2-chloropyridine-1-oxide (VII).

EXAMPLE 9

A mixture of 10.0 g ($3.86 \times 10^{-2}$ m) sulfide VIII and 1.0 g sodium tungstate dihydrate in a solution of 25 ml methanol and 15 ml dichloromethane was heated to 40° and 6.3 g 50% hydrogen peroxide ($9.26 \times 10^{-2}$ m) added during 65 minutes while the temperature of the reaction mixture was maintained in the range 40° to 45°. Stirring and heating at 40° to 45° were continued for an additional 1.5 hours. The dichloromethane was distilled from the reaction vessel at atmospheric pressure. The suspension of sulfone IX in water and methanol remaining in the vessel was cooled to room temperature and 25 ml water was added in order to precipitate additional product and to dissolve the sodium tungstate catalyst. The product, IX, was isolated by filtration, washed with 20 ml water, and dried, yield 9.6 g (85% based on sulfide VIII).

EXAMPLE 10

A mixture of 10.0 g ($3.86 \times 10^{-2}$ m) sulfide VIII and 1.0 g sodium tungstate dihydrate in 40 ml methanol was heated to 40° and 9.0 g 35% hydrogen peroxide ($9.26 \times 10^{-2}$ m) were added during 30 minutes while the temperature of the reaction mixture was maintained in the range 40° to 45°. Stirring and heating at 40° to 45° were continued for an additional 4.3 hours during which sulfide VIII underwent a stepwise oxidation giving, initially, a suspension of sulfoxide intermediate (after about 0.3 hr.) which then converted to a suspension of sulfone IX (after about 4.0 hr.).

The suspension was cooled to room temperature and 40 ml water was added in order to precipitate additional product and to dissolve the sodium tungstate catalyst. The product IX, was isolated by filtration and dried, yield 9.6 g (85% based on sulfide VIII).

Alpha,2,5-trimethylbenzenemethanethiol (V) may be isolated by preparing a solution of thiol V according to Steps A, B and C and extracting the solution with dichloromethane. Fractional distillation of the organic phase affords a 78% yield (based on chloride IV) of thiol V (b.p. 75°–77°, 1.4 mm Hg). The structure of this product was confirmed on the basis of spectral data (NMR and IR) and combustion analysis (Calc. for $C_{10}H_{14}S$: C 72.23; H 8.49. Found: C 72.46; H 8.43). Alkali metal (e.g., sodium, potassium) salts of V may be prepared by contacting V with the appropriate alkali metal hydroxide, as indicated previously. U.S. Pat. No. 3,960,542 discloses that certain 2-thiopyridine N-oxides may be prepared by reacting 2-chloropyridine N-oxide with appropriate mercaptan. The present work (Example 8 in particular) shows that alpha-methylbenzenemethanethiols, for example thiol V, are appropriate mercaptans for coupling with 2-chloropyridine N-oxide. In the case of thiol V the coupling reaction affords 2(1-[2,5-dimethylphenyl]ethylsulfonyl)pyridine N-oxide (VIII), an alternative synthesis of which is disclosed in U.S. Pat. No. 3,960,542 (Example 6).

What is claimed is:

1. (Step F) A method of making (IX) 2-[1-(2,5-dimethylphenyl)ethylsulfonyl]pyridine-1-oxide comprising contacting (VIII) 2-[1-(2,5-dimethylphenyl)ethylthio]-pyridine-1-oxide with an alkali metal tungstate or tungstic acid and hydrogen peroxide in the presence of methanol or methanol and dichloromethane at a temperature of from 35° to 50° and thereafter recovering (IX) 2-[1-(2,5-dimethylphenyl)ethylsulfonyl]pyridine-1-oxide from the reaction mixture.

2. A method of making (IX) 2-[1-(2,5-dimethylphenyl)ethylsulfonyl]pyridine-1-oxide comprising:

(Step E) preparing (VIII) 2-[1-(2,5-dimethylphenyl)ethylthio]pyridine-1-oxide by contacting (VI) alpha,2,5-trimethylbenzenemethanethiol alkali metal salt in aqueous methanol or ethanol with (VII) 2-chloropyridine-1-oxide at a temperature of 50° to 80° whereby (VIII) 2-[1-(2,5-dimethylphenyl)ethylthio]pyridine-1-oxide is formed; and (Step F) thereafter contacting the (VIII) 2-[1-(2,5-dimethylphenyl)ethylthio]pyridine-1-oxide with an alkali metal tungstate or tungstic acid and hydrogen peroxide in the presence of methanol or methanol and dichloromethane at a temperature of from 35° to 50°, and subsequently recovering (IX) 2-[1-(2,5-dimethylphenyl)ethylsulfonyl]pyridine-1-oxide from the reaction mixture.

3. A method of making (IX) 2-[1-(2,5-dimethylphenyl)ethylsulfonyl]pyridine-1-oxide comprising:

(Step C) preparing (V) alpha,2,5-trimethylbenzenemethanethiol by contacting (IV) 2-(1-chloroethyl)-1,4-dimethylbenzene with an alkali metal hydrogen sulfide in aqueous methanol or ethanol at a temperature of 10°–40° to provide a solution of (V) alpha,2,5-trimethylbenzenemethanethiol in aqueous methanol or ethanol;

(Step D) subsequently contacting the (V) alpha,2,5-trimethylbenzenemethanethiol with an alkali metal hydroxide to form (VI) alkali metal salt of (V) alpha,2,5-trimethylbenzenemethanethiol;

(Step E) thereafter contacting the (VI) alpha,2,5-trimethylbenzenemethanethiol alkali metal salt in aqueous methanol or ethanol with (VII) 2-chloropyridine-1-oxide at a temperature of 50° to 80° whereby (VIII) 2-[1-(2,5-dimethylphenyl)ethylthio]pyridine-1-oxide is formed; and (Step F) thereafter contacting the (VIII) 2-[1-(2,5-dimethylphenyl)ethylthio]pyridine-1-oxide with an alkali metal tungstate or tungstic acid and hydrogen peroxide in the presence of methanol or methanol and dichloromethane at a temperature of from 35° to 50°, and subsequently recovering (IX) 2-[1-(2,5-dimethylphenyl)ethylsulfonyl]pyridine-1-oxide from the reaction mixture.

4. A method of making (IX) 2-[1-(2,5-dimethylphenyl)ethylsulfonyl]pyridine-1-oxide comprising:

(Step B) preparing (IV) 2-(1-chloroethyl)-1,4-dimethylbenzene by contacting (II) bis-1-chloroethyl ether with (III) p-xylene and a cosolvent in the presence of sulfuric acid and hydrogen chloride at a temperature of from $-10°$ to $+10°$ whereby (IV) 2-(1-chloroethyl)-1,4-dimethylbenzene is formed;

(Step C) subsequently contacting the (IV) 2-(1-chloroethyl)-1,4-dimethylbenzene with an alkali metal hydrogen sulfide in aqueous methanol or ethanol at a temperature of 10°–40° to provide a solution of (V) alpha,2,5-trimethylbenzenemethanethiol in aqueous methanol or ethanol;

(Step D) subsequently contacting the (V) alpha,2,5-trimethylbenzenemethanethiol with an alkali metal hydroxide to form (VI) alkali metal salt of (V) alpha,2,5-trimethylbenzenemethanethiol;

(Step E) thereafter contacting the (VI) alpha,2,5-trimethylbenzenemethanethiol alkali metal salt in aqueous methanol or ethanol with (VII) 2-chloropyridine-1-oxide at a temperature of 50° to 80° whereby (VIII) 2-[1-(2,5-dimethylphenyl)ethylthio]pyridine-1-oxide is formed; and (Step F) thereafter contacting the (VIII) 2-[1-(2,5-dimethylphenyl)ethylthio]pyridine-1-oxide with an alkali metal tungstate or tungstic acid and hydrogen peroxide in the presence of methanol or methanol and dichloromethane at a temperature of from 35° to 50°, and subsequently recovering (IX) 2-[1-(2,5-dimethylphenyl)ethylsulfonyl]pyridine-1-oxide from the reaction mixture.

5. A method of making (IX) 2-[1-(2,5-dimethylphenyl)ethylsulfonyl]pyridine-1-oxide comprising:

(Step A) preparing (II) bis-1-chloroethyl ether by passing hydrogen chloride into a solution of (III) p-xylene and (I) acetaldehyde or a substance which is decomposable to yield acetaldehyde at a temperature of −10° to +20°, optionally in the presence of a cosolvent, to provide a solution of (II) bis-1-chloroethyl ether in p-xylene or p-xylene and a cosolvent;

(Step B) thereafter contacting the (II) bis-1-chloroethyl ether with (III) p-xylene and a cosolvent in the presence of sulfuric acid and hydrogen chloride at a temperature of from −10° to +10° whereby (IV) 2-(1-chloroethyl)-1,4-dimethylbenzene is formed;

(Step C) subsequently contacting the (IV) 2-(1-chlororethyl)-1,4-dimethylbenzene with an alkali metal hydrogen sulfide in aqueous methanol or ethanol at a temperature of 10°–40° to provide a solution of (V) alpha,2,5-trimethylbenzenemethanethiol in aqueous methanol or ethanol;

(Step D) subsequently contacting the (V) alpha,2,5-trimethylbenzenemethanethiol with an alkali metal hydroxide to form (VI) alkali metal salt of (V) alpha,2,5-trimethylbenzenemethanethiol;

(Step E) thereafter contacting the (VI) alpha,2,5-trimethylbenzenemethanethiol alkali metal salt in aqueous methanol or ethanol with (VII) 2-chloropyridine-1-oxide at a temperature of 50° to 80° whereby (VIII) 2-[1-(2,5-dimethylphenyl)ethylthio]pyridine-1-oxide is formed; and (Step F) thereafter contacting the (VIII) 2-[1-(2,5-dimethylphenyl)ethylthio]pyridine-1-oxide with an alkali metal tungstate or tungstic acid and hydrogen peroxide in the presence of methanol or methanol and dichloromethane at a temperature of from 35° to 50°, and subsequently recovering (IX) 2-[1-(2,5-dimethylphenyl)ethylsulfonyl]pyridine-1-oxide from the reaction mixture.

* * * * *